(12) United States Patent
George et al.

(10) Patent No.: US 11,446,015 B2
(45) Date of Patent: Sep. 20, 2022

(54) SPECIMEN RETRIEVAL BAG

(71) Applicant: Covidien LP, Mansfield, MA (US)

(72) Inventors: Sabastian Koduthully George, Hyderabad (IN); Sridharan Varadhan, Shanghai (CN)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 17/070,285

(22) Filed: Oct. 14, 2020

(65) Prior Publication Data
US 2021/0128129 A1    May 6, 2021

Related U.S. Application Data

(60) Provisional application No. 62/927,743, filed on Oct. 30, 2019.

(51) Int. Cl.
*A61B 17/00* (2006.01)
*A61B 17/072* (2006.01)
*A61L 31/04* (2006.01)

(52) U.S. Cl.
CPC .. *A61B 17/00234* (2013.01); *A61B 17/07292* (2013.01); *A61L 31/041* (2013.01); *A61B 2017/00004* (2013.01); *A61B 2017/00287* (2013.01)

(58) Field of Classification Search
CPC ........ A61B 17/00234; A61B 17/07292; A61B 2017/00004; A61B 2017/00287
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |
| 4,790,812 | A | 12/1988 | Hawkins, Jr. et al. |
| 4,852,586 | A | 8/1989 | Haines |
| 4,927,427 | A | 5/1990 | Kriauciunas et al. |
| 4,977,903 | A | 12/1990 | Haines |
| 4,991,593 | A | 2/1991 | LeVahn |

(Continued)

FOREIGN PATENT DOCUMENTS

| | | |
|---|---|---|
| DE | 25796 C | 1/1884 |
| DE | 3542667 A1 | 6/1986 |

(Continued)

OTHER PUBLICATIONS

European Search Report EP 12191639.9 dated Feb. 20, 2013.
(Continued)

*Primary Examiner* — Mohamed G Gabr
(74) *Attorney, Agent, or Firm* — Carter, DeLuca & Farrell LLP

(57) ABSTRACT

The disclosure is directed to a specimen retrieval bag or a kit including a specimen retrieval bag for use in removing tissue from the body of a patient, in aspects, as part of a minimally invasive surgical procedure. The specimen retrieval bag includes a buttress material affixed to at least a portion of an opening of the specimen retrieval bag.

20 Claims, 8 Drawing Sheets

(56) References Cited

U.S. PATENT DOCUMENTS

| | | |
|---|---|---|
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,396 A | 7/1998 | Mastri et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,865,361 A | 2/1999 | Milliman et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |

(56) References Cited

U.S. PATENT DOCUMENTS

| | | |
|---|---|---|
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,672,206 B2 | 3/2014 | Aranyi et al. |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0236459 A1 | 10/2005 | Gresham |
| 2005/0256425 A1 | 11/2005 | Prusiner |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2007/0213743 A1 | 9/2007 | McGuckin, Jr. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2010/0249646 A1* | 9/2010 | Wynne ............... A61B 10/0096 600/562 |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2016/0310134 A1 | 10/2016 | Contini et al. |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0311964 A1 | 11/2017 | Desai et al. |
| 2017/0325798 A1 | 11/2017 | Prior |
| 2019/0209194 A1* | 7/2019 | Sartor ............... A61B 17/32002 |
| 2020/0305866 A1* | 10/2020 | Knapp ............... A61B 17/295 |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| DE | 10327106 A1 | 12/2004 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2583629 A2 | 4/2013 |
| EP | 2932909 A1 | 10/2015 |
| ES | 2379920 A1 | 5/2012 |
| FR | 1272412 A | 9/1961 |
| GB | 246009 A | 1/1926 |
| WO | 9315675 A1 | 8/1993 |
| WO | 9317630 A1 | 9/1993 |
| WO | 9509666 A1 | 4/1995 |
| WO | 0135831 A1 | 5/2001 |
| WO | 2004002334 A1 | 1/2004 |
| WO | 2004032760 A2 | 4/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2007081601 A2 | 7/2007 |
| WO | 2008114234 A2 | 9/2008 |
| WO | 2009149146 A1 | 12/2009 |
| WO | 2011090862 A2 | 7/2011 |
| WO | 2011090866 A2 | 7/2011 |
| WO | 2013075103 A1 | 5/2013 |
| WO | 2014134285 A1 | 9/2014 |
| WO | 2015134888 A1 | 9/2015 |

(56) References Cited

FOREIGN PATENT DOCUMENTS

| WO | 2015164591 A1 | 10/2015 |
|---|---|---|
| WO | 2017189442 A1 | 11/2017 |
| WO | 2018148744 A1 | 8/2018 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
Extended European Search Report issued in corresponding Appl. No. EP 19170619.1 dated Sep. 19, 2019 (8 pages).
Extended European Search Report issued in Appl. No. 19174966.2 dated Oct. 30, 2019 (10 pages).
Extended European Search Report issued in Appl. No. EP 19197987.1 dated Jan. 8, 2020 (10 pages).
European Search Report dated Jun. 23, 2020, issued in EP Appln. No. 19191319, 11 pages.
Extended European Search Report issued in corresponding Appl. No. EP 20165597.4 dated Aug. 5, 2020 (7 pages).

\* cited by examiner

SPECIMEN RETRIEVAL BAG

CROSS-REFERENCE TO RELATED APPLICATION

This application claims the benefit of and priority to U.S. Provisional Patent Application No. 62/927,743 filed Oct. 30, 2019, the entire disclosure of which is incorporated by reference herein.

TECHNICAL FIELD

The disclosure relates to a specimen retrieval bag for collecting body tissue(s) and/or body fluid(s) during minimally invasive surgical procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of a body cavity. The surgeon can then perform diagnostic and/or therapeutic procedures at the surgical site with the aid of specialized instrumentation, such as forceps, cutters, applicators, and the like, which are designed to fit through additional cannulas.

When removing tumor tissue from a body cavity, it is important that the tumor tissue does not come into contact with healthy or uninvolved tissue. If tumor tissue or tissue parts have to be removed, they may be introduced into a "specimen retrieval bag" at the site where the tumor or diseased tissue has been detached from the surrounding tissue. The specimen retrieval bag is then withdrawn from the body, thereby minimizing contact of the diseased tissue with healthy tissue.

SUMMARY

The disclosure is directed to specimen retrieval bags for use in minimally invasive surgery.

In aspects of the disclosure, a specimen retrieval bag for collecting tissue includes a body defining a cavity and having an open end in communication with the cavity and a buttress material affixed to at least a portion of the open end.

The body may be formed of a material selected from polyethylene, polyurethanes, polyesters, polyethylene terephthalate, thermoplastic elastomers, thermoplastic vulcanizates, silicones, natural rubbers, styrene-butadiene-styrene block copolymers, or combinations thereof.

In some aspects of the present disclosure, the buttress material is positioned along half of a perimeter portion of the open end.

In other aspects, the buttress material is positioned about an entire perimeter portion of the open end.

The buttress material may be affixed to the open end by adhesive bonding, welding, heat laminating, heat-sealing, stitching, or combinations thereof.

In aspects of the present disclosure, the buttress material is formed of a material selected from bioabsorbable materials, non-absorbable materials, natural materials, synthetic materials, or combinations thereof.

Other specimen retrieval bags of the present disclosure for collecting tissue include a body formed of an inner layer and an outer layer adjacent the inner layer, the body defining a cavity having an open end in communication with the cavity, and a buttress material affixed to at least a portion of the inner layer adjacent the open end.

In some aspects of the present disclosure, the open end of the outer layer extends beyond the open end of the inner layer.

The inner layer, the outer layer, or both, are formed of a material selected from polyethylene, polyurethanes, polyesters, polyethylene terephthalate, thermoplastic elastomers, thermoplastic vulcanizates, silicones, natural rubbers, styrene-butadiene-styrene block copolymers, or combinations thereof.

In aspects of the present disclosure, the outer layer includes a mouth at the open end, the mouth possessing a cinch string.

Kits including the specimen retrieval bag of the present disclosure are also provided. In aspects of the present disclosure, a kit includes a surgical stapler and a specimen retrieval bag for collecting tissue, the specimen retrieval bag including a body defining a cavity and having an open end in communication with the cavity and a buttress material affixed to at least a portion of the open end.

BRIEF DESCRIPTION OF THE DRAWINGS

Various aspects are described herein with reference to the drawings wherein.

DETAILED DESCRIPTION

Figure 1:
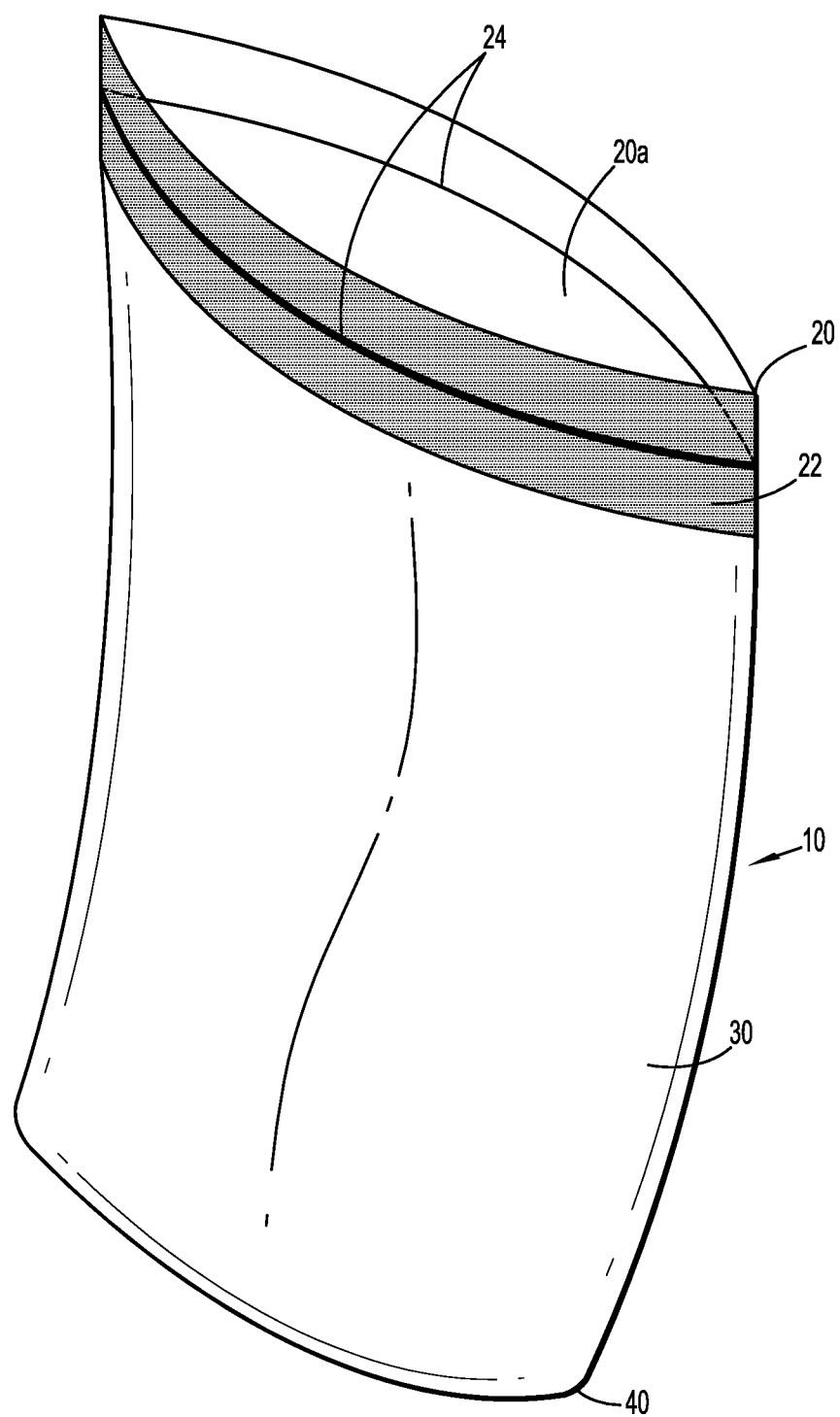
FIG. 1 is a perspective view of a specimen retrieval bag of the disclosure.

As used herein, the term distal refers to that portion of the specimen retrieval bag of the disclosure which is farthest from the user during conventional use, while the term proximal refers to that portion of the specimen retrieval bag of the disclosure which is closest to the user during conventional use.

The disclosure provides specimen retrieval bags suitable for use in any procedure where access to the interior of the body is limited to one or more relatively small incisions, with or without the use of a cannula or other access port, as in minimally invasive procedures. As used herein with reference to the disclosure, minimally invasive surgical procedures encompass laparoscopic procedures and endoscopic procedures, and refer to procedures utilizing scopes or similar devices having relatively narrow operating portions for insertion into a cannula or a small incision in the skin.

Aspects of the disclosure may be modified for use with various methods for retrieving tissue during minimally invasive procedures. Examples of minimally invasive procedures include, for example, cholecystectomies, appendectomies, nephrectomies, colectomies, splenectomies, and the like.

Specimen retrieval bags of the disclosure are made of flexible and durable materials. Materials used to form the specimen retrieval bags are antistatic, pyrogen-free, non-toxic and sterilizable. The specimen bag may be made from any suitable biocompatible material (e.g., nylon, urethane, ripstop nylon or latex) capable of forming a flexible collapsible member, or membrane. The specimen bag may be opaque or clear.

In embodiments, a specimen retrieval bag of the disclosure may be formed of a material such as polyethylene, polyurethanes, polyesters, polyethylene terephthalate, thermoplastic elastomers, thermoplastic vulcanizates, silicones, natural rubbers, styrene-butadiene-styrene block copolymers, or combinations thereof.

Specimen retrieval bags of the disclosure have an open end and a closed distal portion, sometimes referred to herein as a "body". The body defines a cavity into which tissue to be removed from a patient is placed. A buttress material is present at the open end of the specimen retrieval bag. Surgical buttresses may be fabricated from a biocompatible substrate material. Such substrates may be formed of bioabsorbable materials, non-absorbable materials, natural materials, synthetic materials, or combinations thereof.

In embodiments, the surgical buttress may be biodegradable, so that the buttress does not have to be retrieved from the body. The term "biodegradable" as used herein is defined to include both bioabsorbable and bioresorbable materials. By biodegradable, it is meant that the surgical buttress decomposes or loses structural integrity under body conditions (e.g., enzymatic degradation or hydrolysis), or is broken down (physically or chemically) under physiologic conditions in the body such that the degradation products are excretable or absorbable by the body.

Non-limiting examples of materials which may be used in forming a surgical buttress include, but are not limited to, poly(lactic acid), poly(glycolic acid), poly(trimethylene carbonate), poly(dioxanone), poly(hydroxybutyrate), poly(phosphazine), polyethylene terephthalate, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes, and copolymers, block copolymers, homopolymers, blends and combinations thereof.

In embodiments, natural biological polymers may be used in forming a surgical buttress. Suitable natural biological polymers include, but are not limited to, collagen, gelatin, fibrin, fibrinogen, elastin, keratin, albumin, cellulose, oxidized cellulose, hydroxyethyl cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a surgical buttress.

The surgical buttress may also be formed of materials that are porous or non-porous. It should of course be understood that any combination of porous, non-porous, natural, synthetic, bioabsorbable, and/or non-bioabsorbable materials may be used to form a surgical buttress.

Surgical buttresses may have a thickness from about 0.05 mm to about 0.5 mm, in embodiments from about 0.1 mm to about 0.2 mm. These thicknesses are exemplary only and not meant to be limiting. Other suitable thickness as known by a person of skill in the art may be utilized.

In use, tissue to be removed from a patient's body is placed within the specimen retrieval bag. A stapler is fired through the buttress material, thereby closing the open end of the specimen retrieval bag. Firing of the stapler and/or the use of a knife blade associated with the stapler then serves to cut the tissue and seal the buttress, so that the tissue to be removed is enclosed within the specimen retrieval bag. As the stapler fires multiple rows of staples, some staples remain in the patient's body and seal the tissue remaining within the patient's body.

In aspects, linear staplers may be utilized such as, for example, those including EndoGIA™ Reinforced Reload with Tri-Staple Technology™ and other staplers with Tri-Staple™ technology, available through Covidien, (North Haven, Conn.), as well as other anastomosis staplers, such as, for example, EEA™, CEEA™, GIA™, EndoGIA™, and TA™, also available through Covidien.

Methods for attaching the buttress material to the open end of the specimen retrieval bag are within the purview of those skilled in the art and include adhesive bonding, welding, heat laminating, heat-sealing, stitching, combinations thereof, and the like.

Aspects of the disclosure will now be described in detail with reference to the drawings, in which like reference numerals designate identical or corresponding elements in each of the several views. In the following description, well-known functions or constructions are not described in detail to avoid obscuring the disclosure in unnecessary detail.

FIG. 1 illustrates a specimen retrieval bag 10 having a mouth portion 20 defining an opening 20a for receiving tissue and a body 30 defining an interior in communication with the opening 20a. The body 30 is liquid-tight along its edges 40.

The specimen retrieval bag 10 can have a buttress material 22 at the mouth portion 20 to further reduce the chance of a contained tissue spilling from the specimen retrieval bag 10.

Figure 2:
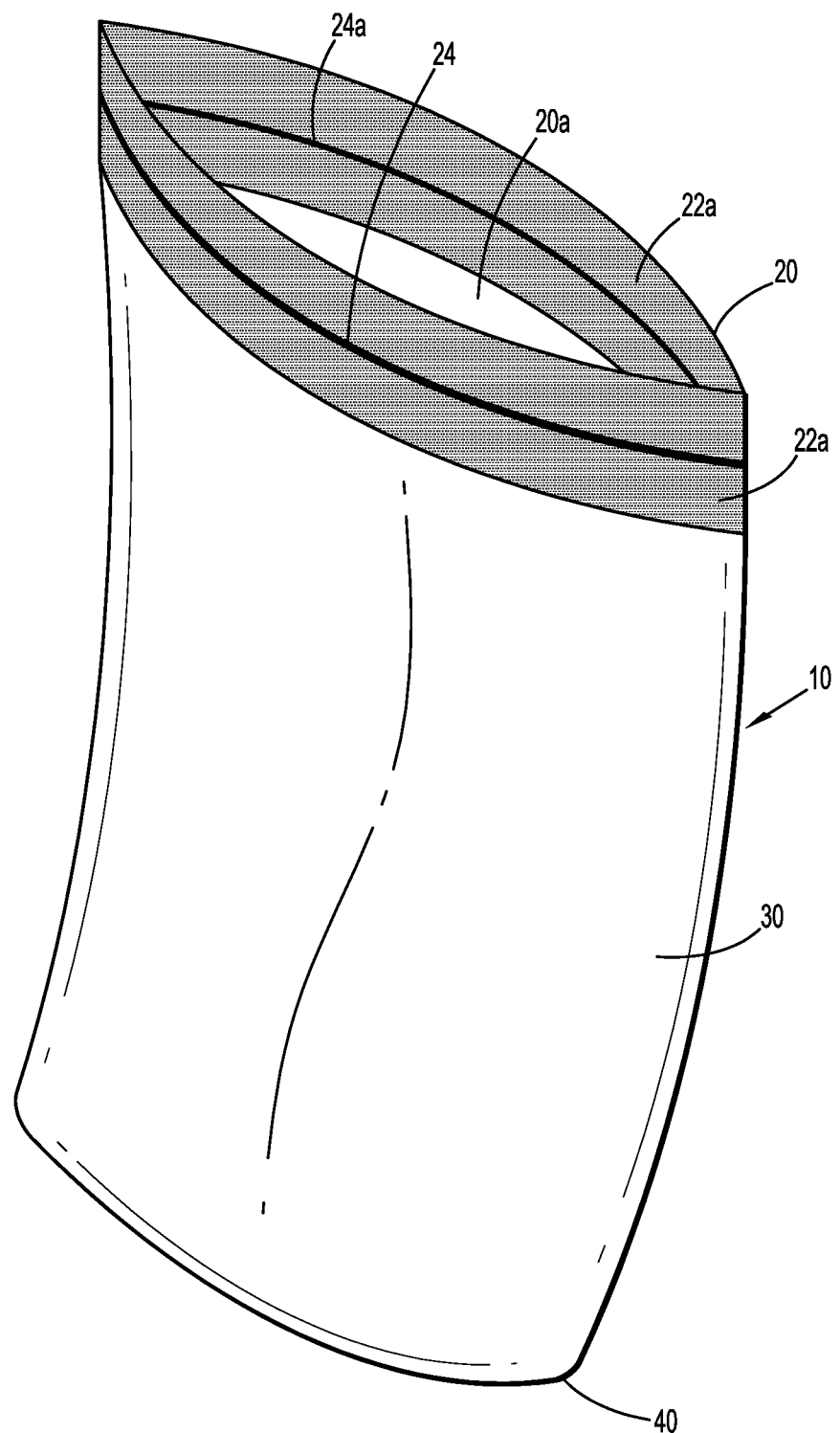
FIG. 2 is a perspective view of an alternate specimen retrieval bag of the disclosure.

The buttress material 22 may be on only half of the mouth portion 20 of the specimen retrieval bag 10. In other aspects, FIG. 2 illustrates buttress material 22a on both halves of the mouth 20 of the specimen retrieval bag 10, thereby fully encompassing the circumference of the mouth 20 of the specimen retrieval bag 10.

In use, specimen retrieval bag 10 is introduced into a patient's body, in aspects through a trocar tube, catheter, cannula, or similar device, and is opened in the patient's body where the tissue to be removed is placed in the specimen retrieval bag 10.

Figure 3:
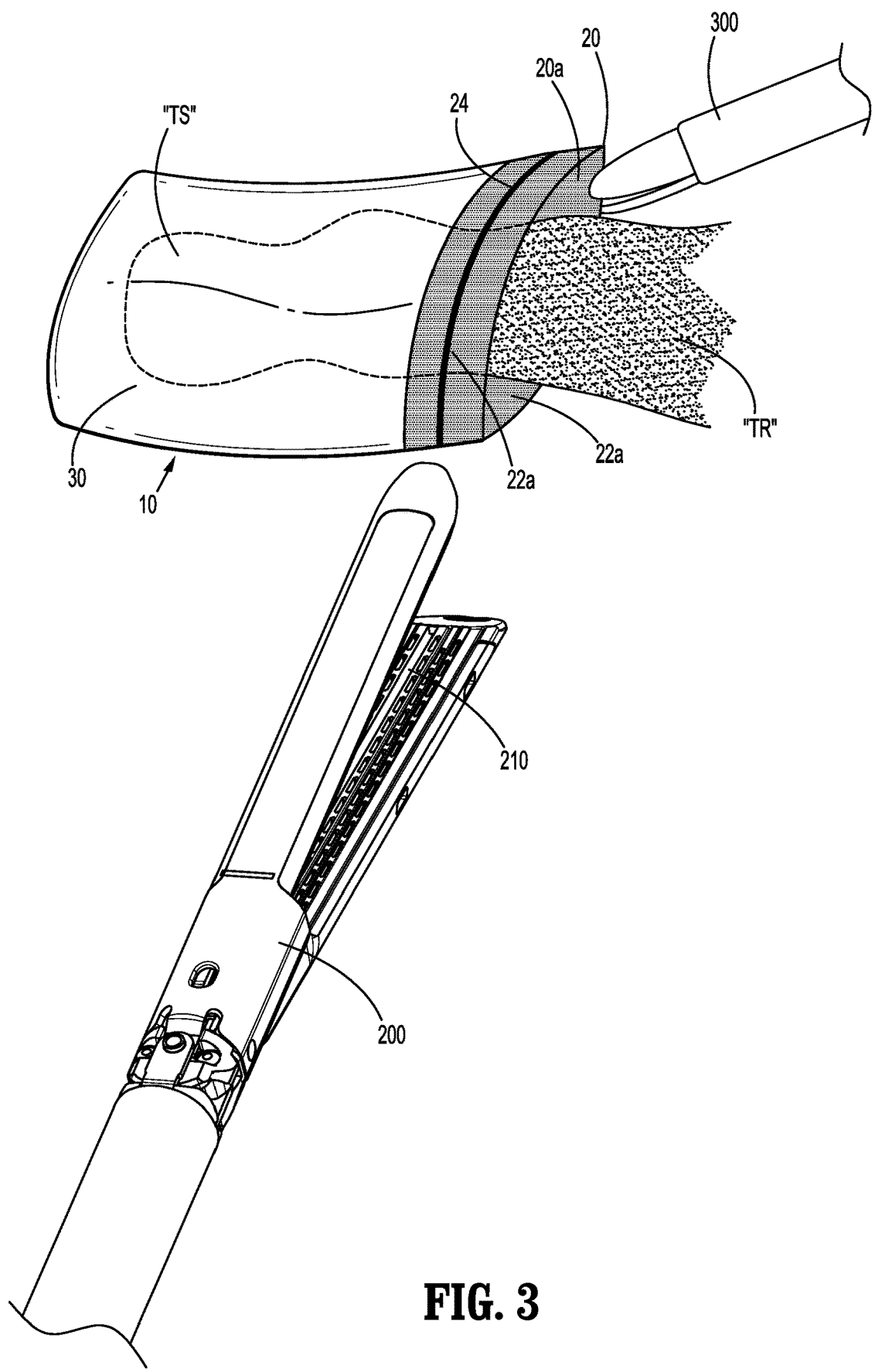
FIG. 3 is a perspective view of the specimen retrieval bag of FIG. 2 in use.

FIG. 3 illustrates the use of a grasper 300 to assist in placement of a tissue specimen "TS" within the specimen retrieval bag 10. Once the tissue specimen "TS" is placed within the specimen retrieval bag 10, the mouth portion 20 of the specimen retrieval bag 10 may be closed by a stapler 200 that staples both the mouth 20 of the specimen retrieval bag 10 and the tissue. After stapling, the tissue specimen "TS" to be removed is enclosed within the specimen retrieval bag 10, at which point a knife blade (not shown) within knife slot 210 of stapler 200 may pass along cut lines 24, 24a (see, FIGS. 1-3) of the buttress material 22a, thereby separating the tissue specimen "TS" within the specimen retrieval bag 10 from the tissue remaining "TR" within the patient's body.

Figure 4:
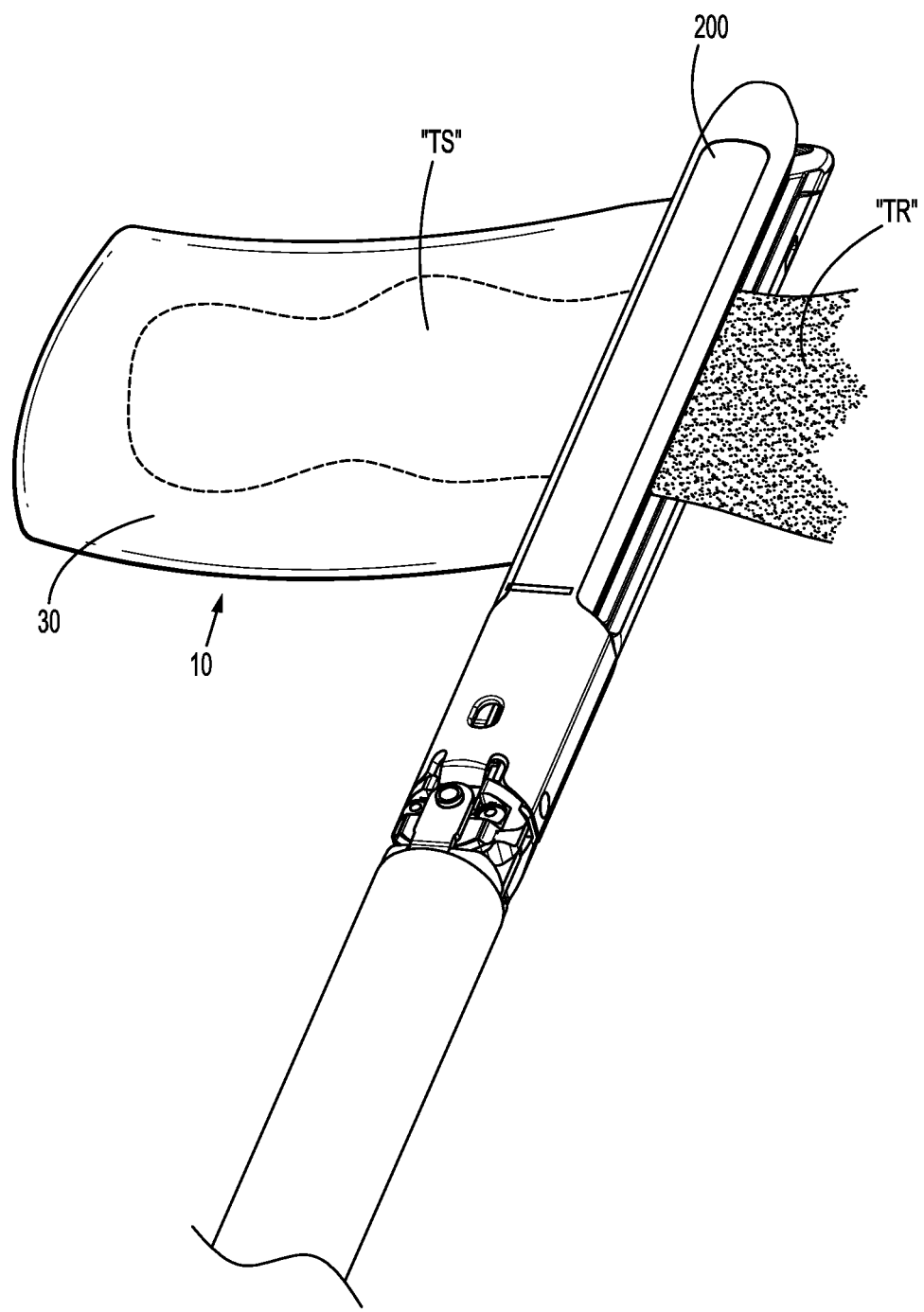
FIG. 4 is a side view of a stapler closing the specimen retrieval bag of FIG. 2.

FIG. 4 illustrates the specimen retrieval bag 10 of the disclosure, with the tissue specimen "TS" to be removed enclosed within the body 30 of the specimen retrieval bag 10 and the tissue remaining "TR" within the patient's body separate therefrom.

Figure 5:
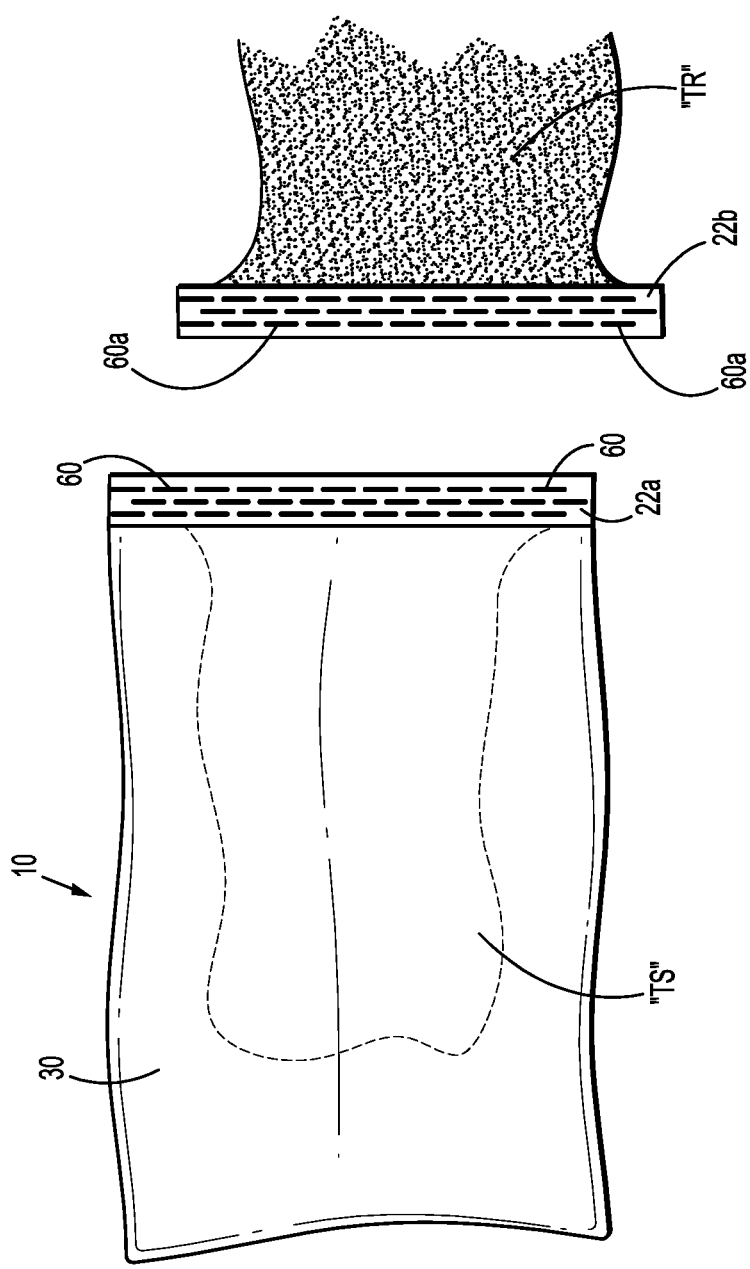
FIG. 5 is a side view of tissue within the specimen retrieval bag of FIG. 2 after stapling.

FIG. 5 depicts the tissue after firing of the stapler. The tissue remaining "TR" within the patient's body has staples 60a and buttress material 22b to seal the tissue remaining "TR" within the patient's body, and the body 30 of the specimen retrieval bag 10 is closed by the staples 60 and buttress material 22a to contain the tissue specimen "TS" within the body 30 of the specimen retrieval bag 10.

Once the mouth portion 20 of the specimen retrieval bag 10 is closed, the specimen retrieval bag 10 can be removed from the patient's body. After the specimen retrieval bag 10 is removed, the tissue "TS" can be removed from the specimen retrieval bag 10 for further examination or the specimen retrieval bag 10 can be discarded.

Figure 6:
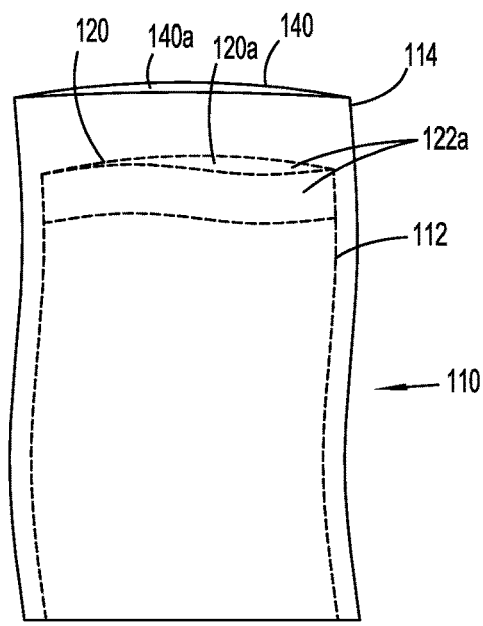
FIG. 6 is a side view of an alternate specimen retrieval bag of the disclosure, having a multi-layer configuration.
Figure 7:
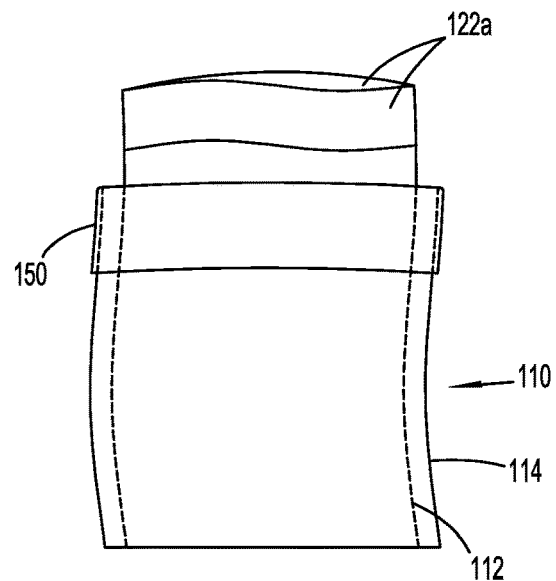
FIG. 7 is a side view of the specimen retrieval bag of FIG. 6, showing folding of an outer layer of the specimen retrieval bag prior to introduction of a tissue sample therein.

An alternate aspect of the specimen retrieval bag of the disclosure is depicted in FIGS. 6-10. FIG. 6 illustrates that a specimen bag 110 of the disclosure may be formed of two layers, an inner layer 112 and an outer layer 114. The inner layer 112 has a mouth 120 forming an opening 120a therein and the outer layer 114 has a mouth 140 forming an opening 140a therein. The outer layer 114 and the inner layer 112 may be of any multi-layer construction within the purview of those skilled in the art. The outer layer 114 may be affixed to the inner layer 112 by any suitable means, including the use of adhesives, welding, lamination, combinations thereof, and the like. In aspects, the outer layer 114 completely encompasses the inner layer 112. The buttress material 122a is at the mouth 120 of the inner layer 112 encompassing opening 120a of the specimen bag 110. FIG. 7 illustrates the mouth 140 of the outer layer 114 of the specimen bag 110 extends beyond the mouth 120 of the inner layer 112. In use, the outer layer 114 may be folded back to form a cuff 150, so that the inner layer 112 with the buttress material 122a at the mouth 120 of the inner layer 112 protrudes therefrom.

Figure 8:
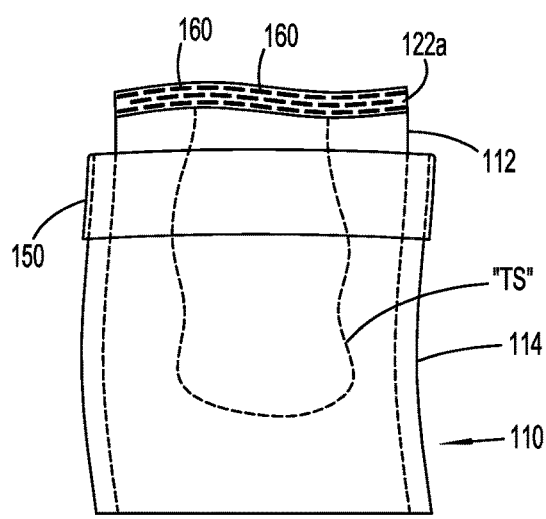
FIG. 8 is a side view of the specimen retrieval bag of FIG. 7 after introduction of a tissue specimen therein.
Figure 9:
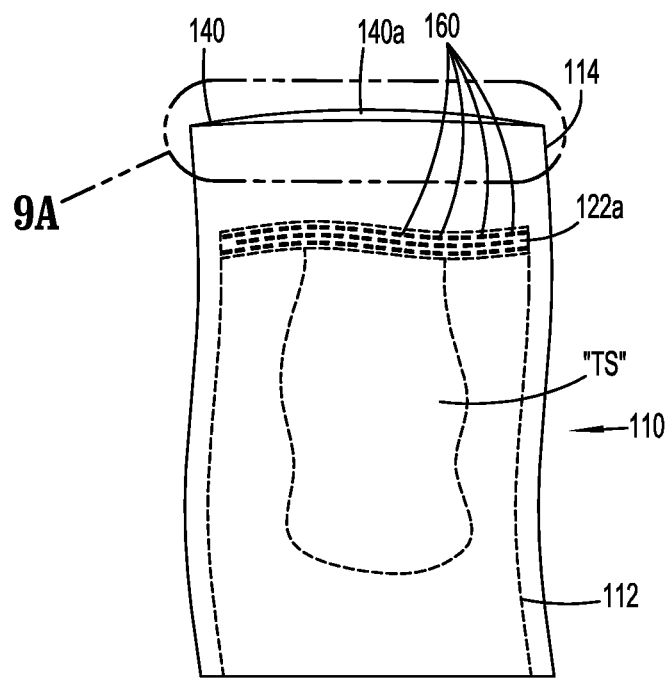
FIG. 9 is a side view of the specimen retrieval bag of FIG. 8, after unfolding the outer layer of the specimen retrieval bag.
Figure 9A:
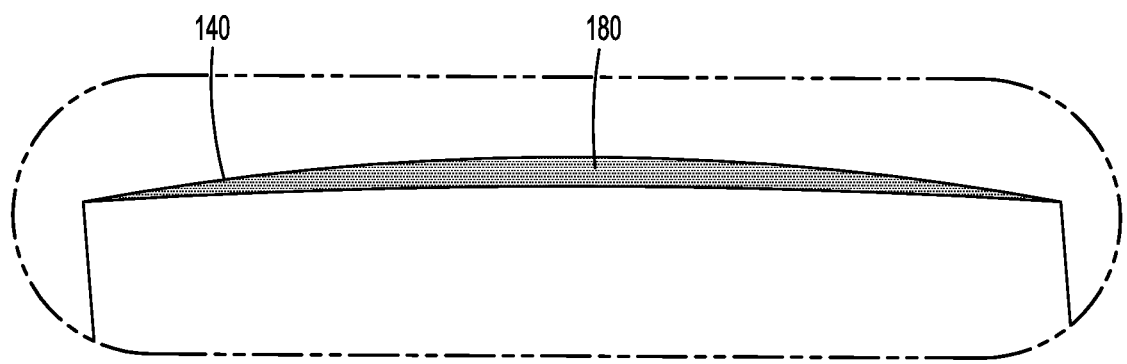
FIG. 9A is an enlarged view of the indicated area of detail shown in FIG. 9.
Figure 10:
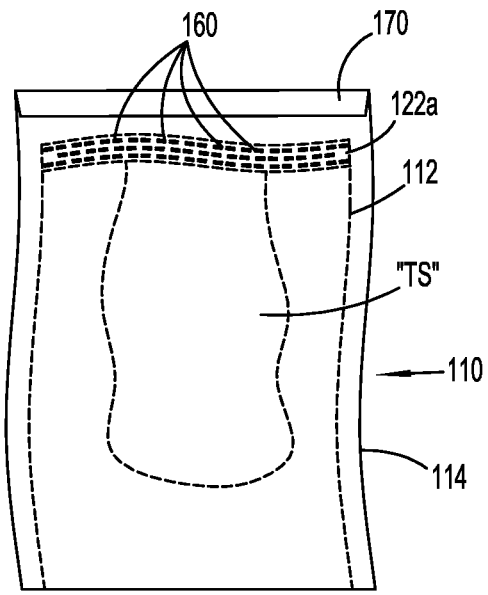
FIG. 10 is a side view of the specimen retrieval bag of FIG. 9, after closing the specimen retrieval bag.
Figure 10A:
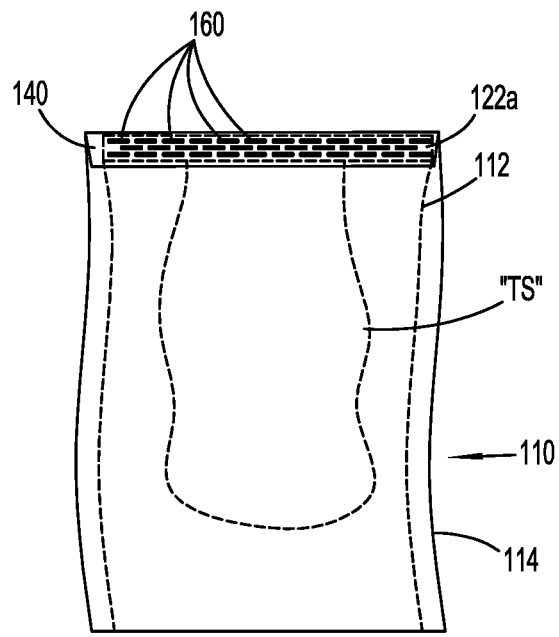
FIG. 10A is a side view of an alternate closure of the specimen retrieval bag of FIG. 9.

As depicted in FIG. 8, a stapler (not shown) is used to close the mouth 120 of the inner layer 114 of the specimen bag 110 with staples 160 and buttress material 122a so that a tissue specimen "TS" to be removed is enclosed within the specimen bag 110. FIG. 9 illustrates that the mouth 140 of the outer layer 114 of the specimen bag 110 may be folded back to its original configuration, and as shown in FIG. 10, the mouth 140 of the outer layer 114 of the specimen bag 110 may then be sealed by any suitable closing mechanism, including a cinch string, adhesive, combinations thereof, and the like. FIG. 9A depicts an adhesive 180 at the mouth 140 of the specimen bag 110 prior to closing the mouth 140 of the specimen bag 110. FIG. 10 depicts a closed end 170 of the outer layer 114 that has been closed by the adhesive 180. In some aspects, as shown in FIG. 10A, the mouth 140 of the outer layer 114 may be closed by adhering mouth 140 of the outer layer 114 to the inner layer 112.

In this way, both the inner layer 112 and the outer layer 114 of the specimen bag 110 are closed, thereby enhancing the seal of the specimen bag 110 to facilitate removal of the tissue specimen "TS" from the patient's body without any further escape of the tissue specimen "TS" or accompanying fluids (not shown) into the patient's body.

Kits of the disclosure may include both the specimen retrieval bags described above, as well as staplers, trocars, catheters, graspers, combinations thereof, and the like.

The specimen retrieval bags of the disclosure provide safe tissue extraction at the end of minimally invasive surgical procedures. Diseased tissue may be removed from the body without seeding of spilled tissue cells inside the body. It is further envisioned that the methods of using the specimen retrieval bags of the disclosure may be modified to accommodate needs of a given procedure and/or the preferences of the surgeon. It is further envisioned that the aspects disclosed herein may be used to remove any tissue or object from the body.

It will be understood that various modifications may be made to the aspects disclosed herein. For example, other methods for introducing specimen retrieval bags of the disclosure into the body of a patient may be used. Additionally, other specimen retrieval bag shapes may be used. Further, the terminology of similar components with the various aspects should not be construed as specific to any particular aspect. Thus, the above description should not be construed as limiting, but merely as exemplifications of preferred aspects. Those skilled in the art will envision other modifications within the scope and spirit of the claims appended hereto.

What is claimed is:

1. A specimen retrieval bag for collecting tissue comprising:
   a body defining a cavity and having an open end in communication with the cavity; and
   a buttress material through which staples are fired into tissue, the buttress material being affixed to at least a portion of the open end,
   wherein in operation of the specimen retrieval bag the staples are fired through the buttress material into the tissue.

2. The specimen retrieval bag of claim 1, wherein the body is formed of a material selected from polyethylene, polyurethanes, polyesters, polyethylene terephthalate, thermoplastic elastomers, thermoplastic vulcanizates, silicones, natural rubbers, styrene-butadiene-styrene block copolymers, or combinations thereof.

3. The specimen retrieval bag of claim 1, wherein the buttress material is positioned along half of a perimeter portion of the open end.

4. The specimen retrieval bag of claim 1, wherein the buttress material is positioned about an entire perimeter portion of the open end.

5. The specimen retrieval bag of claim 1, wherein the buttress material is affixed to the open end by adhesive bonding, welding, heat laminating, heat-sealing, stitching, or combinations thereof.

6. The specimen retrieval bag of claim 1, wherein the buttress material is formed of a material selected from bioabsorbable materials, non-absorbable materials, natural materials, synthetic materials, or combinations thereof.

7. A specimen retrieval bag for collecting tissue comprising:
   a body formed of an inner layer and an outer layer adjacent the inner layer, the body defining a cavity having an open end in communication with the cavity; and
   a buttress material through which staples are fired into tissue, the buttress material being affixed to at least a portion of the inner layer adjacent the open end,
   wherein in operation of the specimen retrieval bag the staples are fired through the buttress material into the tissue.

8. The specimen retrieval bag of claim 7, wherein the open end of the outer layer extends beyond the open end of the inner layer.

9. The specimen retrieval device of claim 7, wherein the inner layer, the outer layer, or both, are formed of a material selected from polyethylene, polyurethanes, polyesters, polyethylene terephthalate, thermoplastic elastomers, thermoplastic vulcanizates, silicones, natural rubbers, styrene-butadiene-styrene block copolymers, or combinations thereof.

10. The specimen retrieval bag of claim 7, wherein the buttress material encompasses half of the open end of the inner layer.

11. The specimen retrieval bag of claim 7, wherein the buttress material encompasses the entire open end of the inner layer.

12. The specimen retrieval bag of claim 7, wherein the buttress material is affixed to the open end of the inner layer by adhesive bonding, welding, heat laminating, heat-sealing, stitching, or combinations thereof.

13. The specimen retrieval bag of claim 7, wherein the buttress material is formed of a material selected from bioabsorbable materials, non-absorbable materials, natural materials, synthetic materials, or combinations thereof.

14. The specimen retrieval bag of claim 7, wherein the outer layer includes a mouth at the open end, the mouth possessing a cinch string.

15. A kit comprising:
   a surgical stapler; and
   a specimen retrieval bag for collecting tissue, the specimen retrieval bag including a body defining a cavity and having an open end in communication with the cavity and a buttress material through which staples are fired into tissue, the buttress material being affixed to at least a portion of the open end,
   wherein in operation of the specimen retrieval bag the staples are fired through the buttress material into the tissue.

16. The kit of claim 15, wherein the body of the specimen retrieval bag is formed of a material selected from polyethylene, polyurethanes, polyesters, polyethylene terephthalate, thermoplastic elastomers, thermoplastic vulcanizates, silicones, natural rubbers, styrene-butadiene-styrene block copolymers, and combinations thereof.

17. The kit of claim 15, wherein the buttress material extends about half of a perimeter portion of the open end.

18. The kit of claim 15, wherein the buttress material extends about an entire perimeter portion of the open end.

19. The kit of claim 15, wherein the buttress material is affixed to the open end by adhesive bonding, welding, heat laminating, heat-sealing, stitching, or combinations thereof.

20. The kit of claim 15, wherein the buttress material is formed of a material selected from bioabsorbable materials, non-absorbable materials, natural materials, synthetic materials, or combinations thereof.

* * * * *